United States Patent [19]

Coll et al.

[11] 4,232,162
[45] Nov. 4, 1980

[54] P-SUBSTITUTED N,N'-BIS-(3-OXAZOLIDINYL-2-ONE)PHOSPHORAMIDES AND PROCESS FOR THE PREPARATION THEREOF

[75] Inventors: Antonio L. P. Coll; José D. Meseguer, both of Barcelona, Spain

[73] Assignee: Antibiotics, S.A., Madrid, Spain

[21] Appl. No.: 927,161

[22] Filed: Jul. 24, 1978

[30] Foreign Application Priority Data

Aug. 11, 1977 [ES] Spain ................................ 461.552

[51] Int. Cl.³ .......................................... C07D 263/32
[52] U.S. Cl. ..................................... 548/111; 424/272
[58] Field of Search ..................... 260/307 C; 548/111

Primary Examiner—Jose Tovar
Attorney, Agent, or Firm—Haseltine, Lake & Waters

[57] ABSTRACT

The present invention is related to a process in which an oxazolidinone is reacted with phosphorus pentachloride and the resulting mixture is reacted with a nucleophilic agent in an inert solvent to give P-substituted N,N'-bis-(3-oxazolidinyl-2-one)phosphoramides having the general formula

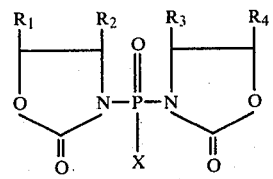

where $R_1$, $R_2$, $R_3$, $R_4$ are each a group selected from among hydrogen, $C_1$–$C_4$ alkyls or an aromatic nucleus and X is a group which may be introduced by nucleophilic substitution. The invention is also related to the compounds thus obtained.

3 Claims, No Drawings

P-SUBSTITUTED N,N'-BIS-(3-OXAZOLIDINYL-2-ONE)PHOSPHORAMIDES AND PROCESS FOR THE PREPARATION THEREOF

SUMMARY OF THE INVENTION

The present invention relates to phosphorus compounds having the following formula:

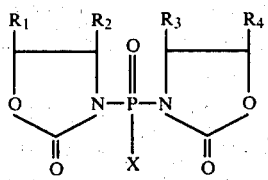

where $R_1$, $R_2$, $R_3$, $R_4$ are a group selected from among hydrogen, alkyls having from one to four carbon atoms or an aromatic nucleus and X is a group which may be introduced by nucleophilic substitution. The invention also relates to a process for the preparation of said compounds.

In particular, the X group introduceable by nucleophilic substitution may be selected from among the halogens and the azide ($N_3$), amino, mercapto, carboxyl and alkoxide groups. In the case of the halogens and the azide ($N_3$) groups, the compounds according to the invention are denominated N,N'-bis-(3-oxazolidinyl-2-one) halogen phosphoramide and N,N'-bis-(3-oxazolidinyl-2-one) phosphorazide and there will be referred to hereinafter with the initials Cl-SPO (X=Cl) and $N_3$-SPO (X=$N_3$). These compounds constitute a family of symmetrical phosphoryl oxazolidinones, to be referred to hereinafter in the abbreviated form of SPO. Furthermore, also for simplicity, the oxazolidinone groups will be abbreviated to OXA, the above compound of Formula (I) being represented by the following expression, to which reference will be made indiscriminately

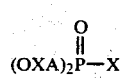

The interest in these substances is founded on the fact that it has now been discovered that they have a surprising capacity for activating functions having wide technical application, such as the carboxyl, amino, hydroxyl and thiol groups among others, and although the activation rate varies for each of them, their wide field of action makes these Formula (I) compounds valuable reagents in synthesis applied to industrial processes and in the technology thereof, such as in the fields of penicillins, cephalosporins, esters having therapeutical application in human and veterinary medicine, etc.

According to the invention, a process for the preparation of P-substituted N,N'-bis-(3-oxazolidinyl-2-one) phosphoramides of the above general Formula (I), wherein X is a group introduceable by nucleophilic substitution, is characterised in that a solution of an inert solvent containing at least two equivalents of an oxazolidinone of the general Formula (II)

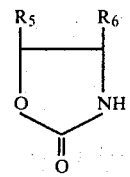

where $R_5$ and $R_6$ may either or both be selected from among the groups $R_1$, $R_2$, $R_3$ and $R_4$ with the meaning given above, is reacted with phosphorus pentachloride and the resulting mixture is reacted with a nucleophilic agent in an inert solvent to obtain a compound of Formula (I), which is isolated by known techniques.

The reaction with phosphorus pentachloride may be effected within a wide range of temperatures ($-15°$ C. to $100°$ C.) and water, alcohol or a carboxylic acid salt may be added to the mixture prior to reacting it with the nucleophilic agent. Sodium azide, alkaline halide, a compound having a hydroxyl, amine, hidrazine or mercapto function, or a salt, preferably triethylamine, of a carboxylic acid may be used as nucleophilic agent, among others.

According to the invention a compound of Formula (II), where $R_5$ and $R_6$ are hydrogen atoms, in an inert solvent such as methylene chloride, acetonitrile or nitromethane, is reacted with phosphorus pentachloride, to give a product of Formula (I), where $R_1$, $R_2$, $R_3$ and $R_4$ are hydrogen and X has the meaning given hereinbefore.

Also according to the invention one equivalent of a compound of Formula (II), were $R_5$ and $R_6$ are hydrogen, in an inert solvent such as methylene chloride is reacted first with phosphorus pentachloride and the resulting N-trichloro-phosphonium-2-oxazolidinone chloride is thereafter reacted with a further equivalent of a compound of Formula (II), where $R_5$ and $R_6$ are preferably hydrogen to obtain a compound of Formula (I), where X has the meaing given hereinbefore.

One object of the invention is the preparation of:
(a) N,N'-bis-(3-oxazolidinyl-2-one)chlorophosphoramides.
(b) N,N'-bis-(3-oxazolidinyl-2-one)azidophosphoramides.
(c) N,N'-bis-(3-oxazolidinyl-2-one)alkoxyphosphoramides, where the alkoxy group comes from an aliphatic, aromatic or heterocyclic alcohol.
(d) N,N'-bis-(3-oxazolidinyl-2-one)aminophosphoramides where the amino group comes from aliphatic, aromatic, heterocyclic bases or carboxyesters of 6-aminopenicillanic or 7-aminocephalosporanic acid.
(e) N,N'-bis-(3-oxazolidinyl-2-one)mercaptophosphoramides, where the mercapto group proceeds from aliphatic, aromatic or heterocyclic thiols.

A further object of the invention is to react a chlorophosphoramide with a carboxylic acid salt to obtain:

1. N,N'-bis-(3-oxazolidinyl-2-one)acyloxyphosphoramide, where the acyloxy group comes from an aliphatic, aromatic or heterocyclic carboxylic acid.
2. N,N'-bis-(3-oxazolidinyl-2-one)acyloxyphosphoramide, where the carboxyl group comes from a carboxylic acid in the C-3 position of a penicillin.
3. N,N'-bis-(3-oxazolidinyl-2-one)acyloxyphosphoramide, where the carboxyl group comes from a carboxylic acid in the C-4 position of a cephalosporin.

4. N,N'-bis-(3-oxazolidinyl-2-one)acyloxyphosphoramides, where the carboxyl group comes from a side chain in C-6 position in a penicillin.

5. N,N'-bis-(3-oxazolidinyl-2-one)acyloxyphosphoramide, where the carboxyl group comes from a side chain in C-7 position in a cephalosporin.

DETAILED DESCRIPTION

Thus, the process according to the invention consists of preparing the Formula (I) compounds following the sequence shown in scheme A through the two alternatives differing in the isolation of the N-trichloro-phosphonium-2-oxazolidinone chloride or directly, using the stoichiometric ratio of two moles of OXA for one of phosphorus halide. In any case, the chloride is exchanged with the azide group or other nucleophilic agent to form compounds of the Formula (I)

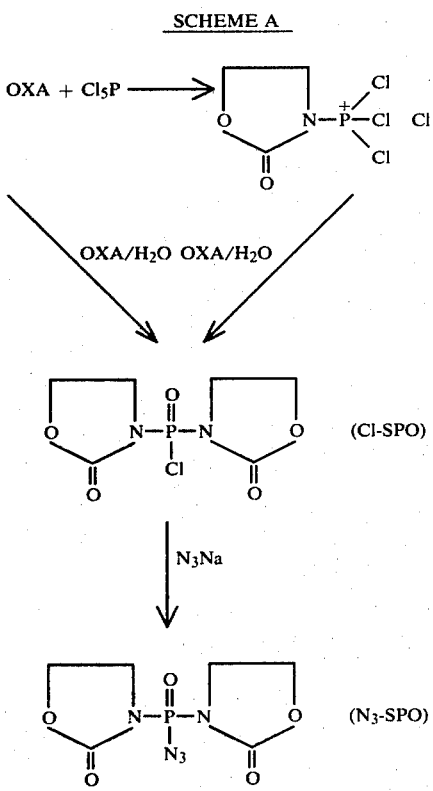

SCHEME A

It will be obvious to the experts in the art that other nucleophilic agents may be represented by X, such as thiocyanate, cyanate, nitrilo, fluoride, bromide and iodide, for example, which would result from the interaction of the Cl-SPO with halogen.

One of the practical ways of preparing the X-SPO comprises reacting a solution of two equivalents of OXA with one mole of phosphorus pentachloride in an inert solvent, conducting the reaction at room temperature (20°-25° C.). Appropriate solvents are methylene chloride, 1,2 methoxyethane, nitromethane and acetonitrile as representatives of non polar aprotic solvents. It is thereafter removed at reduced pressure and the residue is reacted with water at 0°-5° C. in an amount of the order indicated by the stoichiometry of the reaction represented by scheme A.

More convenient is the treatment with water diluted in an inert solvent such as 1,2-dimethoxyethane in which the compound of Formula (I) is insoluble. Also appropriate for this purpose are dioxane, tetrahydrofurane and isopropanol, the chosen one being the one offering the advantages of being a commercially available, low cost product.

A further alternative of preparation is effected, as shown in the same scheme by previously preparing the 3-trihalophosphonium-2-oxazolidinone halide either as specified in Spanish Pat. No. 444.470 or "in situ" in a nitromethane solution, followed by addition of OXA and proceeding as described above. The yields vary from 37% to 80% depending on the solvent, temperature and subsequent hydrolytic treatment and on whether the conversion is conducted in a heterogenous or homogenous phase.

A further possibility is the preparation "in situ" of the reactant, achieved by way of the addition of an adjusted amount of water to the solution containing the reaction raw material.

The Cl-SPO is readily converted into $N_3$-SPO with excellent yield when a solution of nitromethane and an alkali metal, preferably, sodium or potassium, azide, from which it is isolated by removal of the solvent and subsequent recrystallisation.

Part of the interest of the $N_3$-SPO resides in the ease with which it reacts with carboxylates to give the corresponding acyl azides which evolve to isocyanates under heating, thereby opening up a wide range of possibilities of synthesis.

All these compounds are potential, highly significant reactants, the results of which are reflected in scheme B, where the new SPO derivatives indicated therein reveal the importance of the products of the Formula (I), for their applications deriving from this series of intermediate reactants and which are not necessarily isolatable for practical purposes and the technology of the corresponding processes for the preparation of amides, azides, hydrazides and esters. To this end, the following sheme B may be followed.

SCHEME B

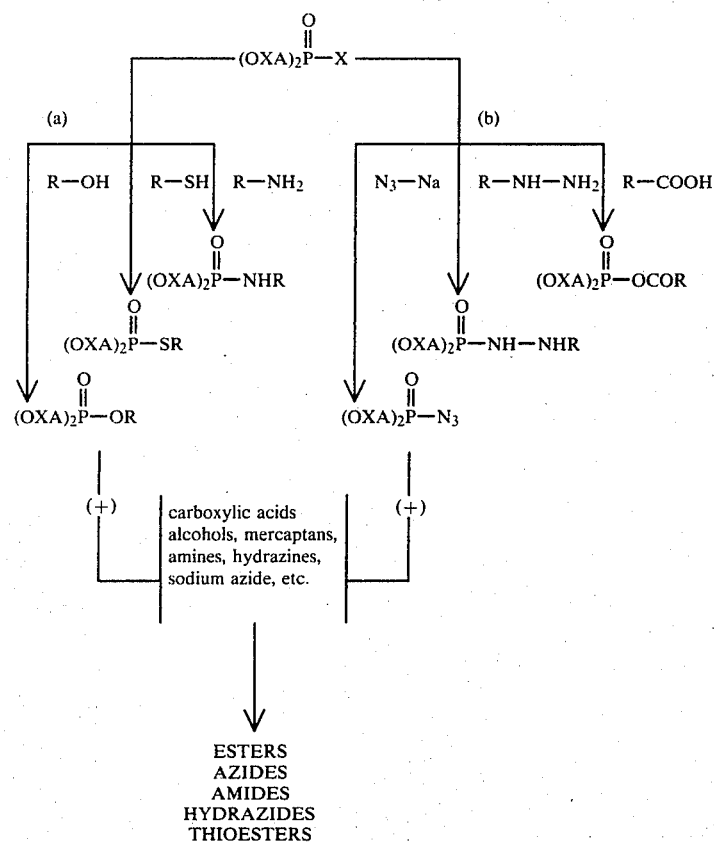

According to sequences (a) and (b) of scheme B, the preference for one or the other depending on the structure and reactivity of the compounds with the groups it is wanted to interchange. When the synthesis of amides and esters is wanted, route (b) is recommendable, in view of the enormous selectivity and speed of the reaction.

Consequently, it may now be understood that the scope of the invention is not restricted to the compounds of Formula I, where X means only halogen or an azide group but that the process for the preparation of phosphorus-substituted N,N'-bis-(3-oxazolidinyl-2-one) phosphoramides extends to compounds of Formula (I) wherein X may be a group selected from among the halogens, azide, amino, alkoxy, mercapto, carboxylate, nitrilo, thiocyanate, cyanate, hydrazino formed in the reaction medium from where they may be chosen on proceeding to their isolation or they may be used directly for the preparation of esters, amides and hydrazides, which may be represented with the initials X-SPO; thus RNH-SPO, R-S-SPO, RCOO-SPO, etc., would be obtained. The preferred one of the oxa groups is 2-oxazolidinone, since it is a low cost commercially available product.

For a better understanding of the object of the present invention, there are described several examples of preparation of X-SPO compounds and their application in the preparation of esters, amides and hydrazides, using known acids, some of which cause difficulties in the formation of derivatives, some of the results of which are given in the following table:

TABLE $$OXA-\underset{X}{\underset{|}{P}}-OXA$$
$$\parallel O$$

| X | REACTANT | SOLVENT | PRODUCT | % YIELD |
|---|---|---|---|---|
| —Cl | Salicyclic acid + aniline | $Cl_2CH_2$ | AMIDE | 87 |
| —$N_3$ | m-nitrobenzoic acid + aniline | $Cl_2CH_2$ | AMIDE | 92 |
| —Cl | m-nitrobenzoic acid + aniline | $Cl_2CH_2$ | AMIDE | 93 |
| —$OCH_3$ | o-nitrobenzoicacid | $Cl_2CH_2$ | ESTER | 51 |
| —$N_3$ | benzoic acid + benzylic acid | DIOXANE | PHENYL CARBOMATE | 60 |

TABLE-continued $$\text{OXA}-\overset{\overset{O}{\|}}{\underset{X}{P}}-\text{OXA}$$

| X | REACTANT | SOLVENT | PRODUCT | % YIELD |
|---|---|---|---|---|
| [2-methylanilino] | benzoic acid | $NO_2-CH_3$ | AMIDE | 56 |
| [benzyl carboxylate, $-OOC-CH_2-C_6H_5$] | benzyl alcohol | $CH_3-CN$ | ESTER | 93 |
| [6-aminopenicillanic acid trimethylsilyl ester, $-HN$-penicillin nucleus-COOSi(CH$_3$)$_3$] | D(−)-α-azidophenyl acetic acid | $Cl_2CH_2$ | AZIDOCILLIN | 55 |
| [phenoxyacetamido-desacetoxycephalosporanate, $-O-H_2C-CO-HN$-cephem-COO$^-$, 3-CH$_3$] | methanol | $Cl_2CH_2$ | ESTER | 82 |
| [7-amino-cephalosporanic acid TMS ester, $-HN$-cephem-CH$_2$-O-CO-CH$_3$, COOSi(CH$_3$)$_3$] | thienylacetic acid | $Cl_2CH_2$ | SODIUM CEPHALOTIN | 47 |
| [phenylmalonate TMS, $-CH(C_6H_5)(COOSi(CH_3)_3)(COO^-)$] | phenol | $Cl_2CH_2$ | MONOPHENYL PHENYL MALONATE | 75 |
| [phenylmalonate TMS, $-CH(C_6H_5)(COOSi(CH_3)_3)(COO^-)$] | 5-indanol | $Cl_2CH_2$ | 5-INDANYL PHENYL MALONATE | 72 |
| [phenylacetamido-penicillanate, $-H_2C-CO-HN$-penicillin-COO$^-$] | α-carboxybenzaldehydic acid | $NO_2-CH_3$ | ESTER | 65 |
| [phenoxyacetamido-penicillanate, $-O-H_2C-CO-HN$-penicillin-COO$^-$] | trichloroethanol | $Cl_2CH_2$ | ESTER | 70 |

Particularly important are the N,N'-bis-(3-oxazolidinyl-2-one) acyloxyphosphoramides which have excellent chemical activity. Moreover, these compounds are easily prepared, for example Cl-SPO is prepared by the action of water on a reaction mixture of the oxa and phophorous pentachloride, followed by reaction with a penicillanic or cephalosporanic, desacetoxycephalosporanic acid and their derivatives, by previously forming with them an amine salt, preferably triethylamine, in an inert solvent such as methylene chloride. The reaction may produce a solution or precipitate of the acyloxyphosphoramide, isolatable in either case by evaporation of the solvent or precipitation with n-heptane in the case of a solution and final filtration. All show characteristic IR spectra with respect to the position of the carbonyl function of the carboxyl group, apart from the reading corresponding to the beta-lactam nucleus, and the reading due to the presence of phosphorus in the molecule.

In view of their illustrative nature, the examples described hereinafter are deemed to be devoid of any limitative effect with respect to the scope of legal protection applied for.

EXAMPLE 1

N,N'-bis-(3-oxazolidinyl-2-one)chlorophosphoramide (Cl-SPO)

To a solution of 5.4 g (6.21 cmoles) of 2-oxazolidinone in 60 ml of methylene chloride at 20° C., there was added 6.24 g (3 cmoles) of phosphorus pentachloride in one go, to give a yellow coloured solution giving an abundant precipitate after 5 minutes. It was stirred for 12 hours at 20°–25° C. and for 1 hour at reflux, to obtain an appreciable solution which was not total. The solvent was thereafter removed under reduced pressure to give an oil which was cooled to 0° C. and to which 20 ml of very cold water was added with vigorous stirring. The mixture was filtered quickly and washed with 10 ml of 1,2-dimethoxyethane. Yield: 2.8 g (37%). Melting point 191°–3° C. Microanalysis ($C_6H_8O_5N_2$ Cl P): Calculated: C 28.27; H 3.14; N 10.99. Found: C 28.19; H 3.08; N 10.89.

EXAMPLE 2

N,N'-bis-(3-oxazolidinyl-2-one)chlorophosphoramide (Cl-SPO)

7 g (8.05 cmoles) of 2-oxazolidinone were dissolved in 80 ml of methylene chloride at 20° C. and 9 g (4.3 cmoles) of phosphorus pentachloride were added at one go to give a total solution and subsequent precipitation. The mixture was stirred for 22 hours at 20°–25° C., the solvent was driven off at reduced pressure and there was obtained an oil to which 10 ml of 1,2-dimethoxyethane were added. The mixture was chilled to 0° C. Subsequently, over a period of 5 minutes a solution of 5 ml of 1,2-dimethoxyethane and 4 ml of water was added dropwise. The temperature was held to between 0° and 5° C. The solid obtained was filtered and washed with 10 ml of 1,2-dimethoxyethane. Yield: 6.0 g (55%).

EXAMPLE 3

N,N'-bis-(3-oxazolidinyl-2-one)chlorophosphoramide (Cl-SPO)

To a solution of 34.8 g (40 cmoles) of 2-oxazolidinone in 380 ml of nitromethane there were added at one go 41.7 g (20 cmoles) of phosphorus pentachloride, to give a solution which was stirred for 4 hours at 20°–25° C. and for a further hour at 40°–45° C. After chilling to 0° C., there was added a mixture of 15 ml of water and 50 ml of 1,2-dimethoxyethane over a period of 5 minutes. Thereafter the solvent was driven off at reduced pressure to give a white residue which was crystallised with the addition of 10 ml of 1,2-dimethoxyethane. It was filtered, washed with 1,2-dimethoxyethane, vacuum dried at 50° C. to yield 40.64 g (80%) of the compound of the title, with a correct microanalysis.

EXAMPLE 4

N,N'-bis-(3-oxazolidinyl-2-one)chlorophosphoramide (Cl-SPO)

Following Example 3 and replacing the nitromethane with acetonitrile, a yield of 65% (32.02 g) was obtained.

EXAMPLE 5

N,N'-bis-(3-oxazolidinyl-2-one)chlorophosphoramide (Cl-SPO)

Following Example 3 and replacing the water by 15 ml of methanol, a yield of 54% (27.43 g) was obtained.

EXAMPLE 6

N,N'-bis-(3-oxazolidinyl-2-one)chlorophosphoramide (Cl-SPO)

Following Example 2 and replacing the aqueous solution by a solution of 2.4 g of glacial acetic acid and 5.6 ml of triethylamine in 10 ml of 1,2-dimethoxyethane, a yield of 50% (5.46 g) was obtained.

EXAMPLE 7

N,N'-bis-(3-oxazolidinyl-2-one)chlorophosphoramide (Cl-SPO)

Following Example 2 and replacing the methylene chloride by acetonitrile and the 1,2-dimethoxyethane by dioxane, a yield of 60% (6.44 g) was obtained.

EXAMPLE 8

N,N'-bis-(3-oxazolidinyl-2-one)chlorophosphoramide (Cl-SPO)

Following Example 3 and replacing the 1,2-dimethoxyethane by tetrahydrofuran, a yield of 78% (39.62 g) was obtained.

EXAMPLE 9

N,N'-bis-(3-oxazolidinyl-2-one)chlorophosphoramide (Cl-SPO)

Following Example 2 and replacing the 1,2-dimethoxyethane by isopropanol, a yield of 35% (2.67 g) was obtained.

EXAMPLE 10

N,N'-bis-(3-oxazolidinyl-2-one)chlorophosphoramide (Cl-SPO)

0.87 g (1 cmole) of 2-oxazolidinone were dissolved in 10 ml of methylene chloride at 20° C. and 2.08 g (1 cmole) of phosphorus pentachloride were added at one go. After 5 minutes stirring, there was an abundant precipitation. Thereafter a further cmole of 2-oxazolidinone (0.87 g) was added and the process according to Example 2 was followed, the compound of the title being isolated with a similar yield.

EXAMPLE 11

N,N'-bis-(3-oxazolidinyl-2-one)chlorophosphoramide (Cl-SPO)

1.74 g (2 cmoles) of 2-oxazolidinone were dissolved in 10 ml of acetonitrile and 2.08 g of phosphorus pentachloride were added at one go, to give a yellow coloured total solution. The solution was stirred for 12 hours at 20°–25° C. and for one hour under reflux. Thereafter it was chilled to 0° C. and 0.2 ml of water (approximately 1 cmole) was added dropwise, to give 1 cmole of Cl-SPO (2.54 g).

EXAMPLE 12

N,N'-bis-(3-oxazolidinyl-2-one)azidophosphoramide (N$_3$-SPO)

5.08 g of Cl-SPO (2 cmoles) were dissolved in 50 ml of nitromethane at 40° C. 1.95 g (3 cmoles) of sodium azide were added. The mixture was stirred for 3 hours at 70° C. It was filtered, the solvent was driven off at reduced pressure at 50° C. to give a white solid; weight 5.6 g. Yield 97%. This was recrystallised in ethanol or 1,2-dimethoxyethane. Melting point: 97°–99° C. IR: N$_3$ band at 2,190 cm$^{-1}$ and carbonyl band at 1,770 cm$^{-1}$. Microanalysis (C$_6$H$_8$O$_5$N$_5$P): Calculated: C 27.58%; H 3.06%; N 26.81%; Found: C 27.41%; H 2.97%; N 26.43%.

EXAMPLE 13

N,N'-bis-(3-oxazolidinyl-2-one)azidophosphoramide (N$_3$-SPO)

Following Example 12 and replacing the nitromethane by 75 ml of acetonitrile, 4.75 g of N$_3$-SPO were obtained, with a 91% yield. A sample of 1.3 g of N$_3$-SPO was taken with 0.61 g of benzoic acid, 0.7 ml of triethylamine (TEA) in 16 ml of tert-butanol. The mixture was stirred under reflux for 6 hours; the IR of the thus obtained solution showed the absence of the N$_3$ band. Water was added to the solution, it was stirred and 25 ml of benzene was added. The solution was washed with water, a saturated bicarbonate solution and finally with water. The benzene was dried over sodium sulphate. The solution was evaporated to dryness at reduced pressure. The solid obtained was recrystallised in n-hexane to give tert-butyl phenylcarbamate, melting point 134°–136° C. Yield 70%. IR: carbonyl band at 1690 cm$^{-1}$ and NH band at 3320 cm$^{-1}$.

Following the above technique, and replacing the benzoic acid by 0.84 g of paranitrobenzoic acid, tert-butyl paranitrophenylcarbamate was obtained. Melting point 112°–114° C. Yield 65%. IR: NH band at 3280 cm$^{-1}$ and carbonyl band at 1690 cm$^{-1}$.

EXAMPLE 14

N,N'-bis-(3-oxazolidinyl-2-one)acetyloxyphosphoramide 1.27 g of Cl-SPO (0.5 cmole) were suspended in 10 ml of methylene chloride and a solution of 0.30 ml of glacial acetic acid and 0.7 ml of triethylamine in 5 ml of methylene chloride was added thereto. The mixture was stirred for 30 minutes at 20°–25° C. without obtaining complete solution. The carbonyl band of the SPO at 1770 cm$^{-1}$ was missing from the IR spectrum of the soluble fraction (performed in solution) whereas there were bands at 1760 and 1735 cm$^{-1}$, corresponding to the compounds of the title. The insoluble fraction was filtered out to give 0.7 g of the above product having an IR spectrum (in methylene chloride solution) superimposable to the one cited above. Melting point: 240°–2° C.

To obtain the acetanilide, there was added to the suspension (without filtering, therefore), a solution of 0.5 ml of aniline (approximately 0.5 cmole) in 5 ml of methylene chloride, the mixture was stirred for 2 hours in a water-ice bath and a solution of 0.7 ml of TEA (0.5 cmole) in 2 ml of methylene chloride was added gradually. The final pH was 4.5. The mixture was acidulated to pH 1.5. The organic phase was drawn off, dried over sodium sulphate and dried out to give the acetanilide with a yield of 94%. Melting point: 114° C.

EXAMPLE 15

N,N'-bis-(3-oxazolidinyl-2-one)pivalyloxyphosphoramide

Following Example 14 and replacing the acetic acid with 0.51 g of pivalic acid, a complete solution was obtained, the IR spectrum of which shows the absence of the carbonyl band at 1770 cm$^{-1}$ and the appearance of bands at 1760 and 1730 cm$^{-1}$.

Thereafter there was added a solution of 0.5 ml aniline (approximately 0.5 cmole) in 5 ml of methylene chloride and the process followed as described in Example 14. After filtering and drying, the anilide was obtained with a 78% yield. Melting point 129° C.

EXAMPLE 16

N,N'-bis-(3-oxazolidinyl-2-one)3,5-dinitrobenzyloxyphosphoramide 1.27 g (0.5 cmole) of Cl-SPO were suspended in 10 ml of nitromethane and a solution of 1.06 g (0.5 cmole) of 3,5-dinitrobenzoic acid and 0.7 ml of triethylamine in 5 ml of nitromethane was added thereto. The mixture was stirred for 15 minutes at 20°–25° C., whereby complete solution was obtained.

The IR spectrum in solution showed absence of the carbonyl band at 1770 cm$^{-1}$ and the appearance of bands at 1775 and 1735 cm$^{-1}$. Thereafter a solution of 0.5 ml aniline (approximately 0.5 cmole) in 5 ml of nitromethane was added thereto and the process was continued as per Example 14. The anilide was obtained with a 90% yield and had a melting point of 234° C.

EXAMPLE 17

N,N'-bis-(3-oxazolidinyl-2-one)benzoyloxyphosphoramide

Following Example 14 and replacing the acetic acid with 0.62 g of benzoic acid (0.5 cmole), a complete solution was obtained having an IR spectrum showing absence of the carbonyl band at 1770 cm$^{-1}$ and the appearance of bands at 1730 and 1755 cm$^{-1}$.

Thereafter there was added a solution of 0.5 ml of aniline (approximately 0.5 cmole) in 5 ml of methylene chloride and the process was continued as per Example 14. After filtering and drying, the anilide was obtained with a yield of 85%. Melting point: 162°–4° C.

EXAMPLE 18

N,N'-bis-(3-oxazolidinyl-2-one)-chloroacetylaminodesacetoxycephalosporanoyloxyphosphoramide Following Example 14 and replacing the acetic acid with 1.46 g of chloroacetylamino-desacetoxycephalosporanic acid, a solution was obtained having an IR spectrum with bands at 1780 cm$^{-1}$ (beta-lactam), 1755 and 1735 cm$^{-1}$.

EXAMPLE 19

N,N'-bis-(3-oxazolidinyl-2-one)chloroacetamidepenicillanoyloxyphosphoramide

Following Example 14 and replacing the acetic acid with 1.45 g of 6-chloroacetylamido-penicillanic acid, a solution was obtained having an IR spectrum with bands at 1780 cm$^{-1}$ (beta-lactam), 1760 and 1740 cm$^{-1}$.

EXAMPLE 20

N,N'-bis-(3-oxazolidinyl-2-one)thienylacetamidecephalosporanoyloxyphosphoramide

Following Example 14 and replacing the acetic acid with 1.98 g of thienylacetamido-cephalosporanic acid, a solution was obtained having an IR spectrum with bands at 1780 cm$^{-1}$ (beta-lactam), 1760 and 1740 cm$^{-1}$.

EXAMPLE 21

N,N'-bis-(3-oxazolidinyl-2-one)-N-phenylaminophosphoramide

To a suspension of 1.27 g of Cl-SPO (0.5 cmole) in 10 ml of methylene chloride, there was added a solution of 1 ml of aniline and 0.7 ml of triethylamine in 10 ml of methylene chloride at 20° C. After stirring for five hours at 20°–25° C., a complete solution was obtained. The organic phase was extracted with acid water, dried over anhydrous sodium sulphate and concentrated at reduced pressure. The residue gave 0.9 g of the compound of the title. Yield 56%. Melting point: 195°–8° C. IR% N-H band at 3190 cm$^{-1}$ and carbonyl band at 1770 cm$^{-1}$. A further solution of 0.62 g of benzoic acid and 0.7 ml of triethylamine in 5 ml of methylene chloride was added to the N-phenylaminophosphoramide solution, was stirred for 48 hours at 20°–25° C. After extraction with acid water at 0°–5° C., the corresponding anilide was obtained with a 51% yield. Melting point: 162°–4° C.

EXAMPLE 22

N,N'-bis-(3-oxazolidinyl-2-one)phenylhydrazinophosphoramide

To a suspension of 2.54 g (1 cmole) of Cl-SPO in 10 ml of methylene chloride there was gradually added a solution of 1.08 g (1 cmole) of phenylhydrazine in 5 ml of methylene chloride, thereafter 1.4 ml of triethylamine was poured in and the mixture was stirred for 60 minutes at room temperature. A solution of the compound of the title was obtained.

To the above solution there was added 1 cmole of triethylamine benzoate in 10 ml of methylene chloride. Stirring was continued for 3 hours at room temperature and subsequently phenylhydrazide (59%) was isolated. Melting point: 108° C.

EXAMPLE 23

N,N'-bis-(3-oxazolidinyl-2-one)methoxyphosphoramide 1.27 g of Cl-SPO were suspended in 10 ml of methylene chloride and there was added thereto a solution of 6 ml of methanol and 0.7 ml of triethylamine. Stirring was continued for 90 minutes at 20°–25° C., whereby an acid solution was obtained at 0°–5° C. The organic phase was dried over anhydrous sodium sulphate, the solvent was driven off under reduced pressure to give 0.8 g of methyl ester. Yield: 64%. Melting point: 83°–84° C. IR: Carbonyl band at 1760 cm$^{-1}$.

After solubilisation of the Cl-SPO, the following solution was added: 1.06 g of 3,5-dinitrobenzoic acid and 0.7 ml of triethylamine in 5 ml of methylene chloride. Stirring was continued for 72 hours at 20°–25° C. and the organic phase was extracted with acid water. It was dried over sodium sulphate and the solvent was driven off at reduced pressure to give 0.52 g of the ester. Yield 52%. Melting point: 105°–6° C. IR: Carbonyl band at 1725 cm$^{-1}$.

EXAMPLE 24

N,N'-bis-(3-oxazolidinyl-2-one)ethylthiophosphoramide 2,54 g (1 cmole) of Cl-SPO were dissolved in 10 ml of nitromethane at 40° C. 1.26 g (1.5 cmoles) of sodium thioethylate were added. Stirring was continued for 3 hours at 70° C. The mixture was filtered to give a solution of ethylthiophosphoramide, to which there was added dropwise a solution of 1 cmole of triethylamine acetate in 5 ml of nitromethane. Stirring was continued for 2 hours at 20°–25° C., to give the ester with a 62% yield. Boiling point: 116°–7° C. Density: 0.9755.

EXAMPLE 25

N,N'-bis-(4-methyl-3-oxazolidinyl-2-one)chlorophosphoramide

Following Example 1 and replacing the 2-oxazolidinone with 4-methyl-2-oxazolidinone, the compound of the title was isolated with a similar yield. It was characterised by its IR spectrum, with specific readings due to the carbonyl and the presence of phosphorus.

EXAMPLE 26

N,N'-bis-(5-ethyl-3-oxazolidinyl-2-one)chlorophosphoramide

Following Example 3 and replacing the 2-oxazolidinone with 5-ethyl-2oxazolidinone, the compound of the title was isolated with a similar yield. It was characterised by specific readings in the IR spectrum, due to the carboxyl and the presence of phosphorus.

EXAMPLE 27

N,N'-bis-(5-methyl-4-ethyl-3-oxazolidinyl-2-one)-chlorophosphoramide

Following Example 3 and replacing the 2-oxazolidinone with 5-methyl-4-ethyl-2-oxazolidinone, the compound of the title was isolated with a similar yield. It was characterised by the IR readings due to the carbonyl and the phosphorus.

EXAMPLE 28

N,N'-bis-(5-phenyl-3-oxazolidinyl-2-one)chlorophosphoramide

Following Example 3 and replacing the 2-oxazolidinone with 5-phenyl-2-oxazolidinone, the compound of the title was isolated with a similar yield. It was characterised by the IR readings due to the carbonyl and the phosphorus.

What we claim is:

1. P-substituted N,N'-bis-(3-oxazolidinyl-2-one) phosphoramides of the Formula (I)

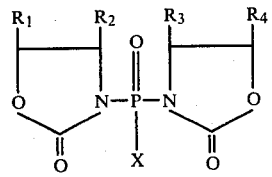

where $R_1$, $R_2$, $R_3$ and $R_4$ represent a group selected from among hydrogen, alkyls having from one to four carbon atoms or an aromatic nucleus and X is halogens.

2. A compound according to claim 1 which is N,N'-bis-(3-oxazolidinyl-2-one)chlorophosphoramide.

3. P-substituted N',N-bis(3-oxazolidinyl-2-one phosphoramides according to claim 1 where $R_1$, $R_2$, $R_3$ and $R_4$ are hydrogen and X is chloro.

* * * * *